(12) United States Patent
Falgout

(10) Patent No.: US 12,239,139 B2
(45) Date of Patent: Mar. 4, 2025

(54) SHRIMP PROCESSING SYSTEM

(71) Applicant: Laitram, L.L.C., Harahan, LA (US)

(72) Inventor: Byron M. Falgout, River Ridge, LA (US)

(73) Assignee: Laitram, L.L.C., Harahan, LA (US)

( * ) Notice: Subject to any disclaimer, the term of this patent is extended or adjusted under 35 U.S.C. 154(b) by 409 days.

(21) Appl. No.: 17/797,033

(22) PCT Filed: Feb. 9, 2021

(86) PCT No.: PCT/US2021/017209
§ 371 (c)(1),
(2) Date: Aug. 2, 2022

(87) PCT Pub. No.: WO2021/178111
PCT Pub. Date: Sep. 10, 2021

(65) Prior Publication Data
US 2023/0067525 A1   Mar. 2, 2023

Related U.S. Application Data

(60) Provisional application No. 62/985,014, filed on Mar. 4, 2020.

(51) Int. Cl.
*A22C 29/00* (2006.01)
*A22C 29/02* (2006.01)

(52) U.S. Cl.
CPC .......... *A22C 29/005* (2013.01); *A22C 29/026* (2013.01)

(58) Field of Classification Search
CPC .............................. A22C 29/005; A22C 29/026
USPC ............................................................ 452/2
See application file for complete search history.

(56) References Cited

U.S. PATENT DOCUMENTS

| | | | |
|---|---|---|---|
| 4,972,093 A | 11/1990 | Cochran et al. | |
| 5,164,795 A | 11/1992 | Conway | |
| 5,839,952 A * | 11/1998 | Pollingue | A22C 29/026 452/8 |
| 6,410,872 B2 | 6/2002 | Campbell et al. | |
| 6,808,448 B1 | 10/2004 | Kanaya et al. | |

(Continued)

FOREIGN PATENT DOCUMENTS

| JP | 2019-204168 A | 11/2019 |
|---|---|---|
| KR | 10-2006-0123518 A | 12/2006 |

(Continued)

*Primary Examiner* — Richard T Price, Jr.
(74) *Attorney, Agent, or Firm* — James T. Cronvich

(57) ABSTRACT

A shrimp processing system conveys raw peeled shrimps to an imaging chamber in which shrimp bits and shrimps with residual shell are detected and diverted from the stream of acceptable shrimps allowed to pass on to downstream processing. An ultraviolet (UV) light source in the imaging chamber is constantly on. A visual inspection system takes images of the passing stream of shrimp when a white-light source is turned on to illuminate an exposure region to detect bits, clumps of shrimps, and acceptable individual shrimps. The visual inspection system takes images of the passing stream when the white-light source is turned off and the exposure region is subjected only to ultraviolet radiation. The visual inspection system detects shrimps with residual shell in the UV images. Shrimp bits and shrimps with residual shell are diverted from the stream of shrimps by air jet nozzles to corresponding reject destinations.

18 Claims, 5 Drawing Sheets

(56) References Cited

U.S. PATENT DOCUMENTS

| | | |
|---|---|---|
| 7,137,696 B2 | 11/2006 | Siegel |
| 7,616,733 B2 | 11/2009 | Sommer et al. |
| 9,174,245 B2 | 11/2015 | Blanc et al. |
| 9,557,265 B2 | 1/2017 | Balthasar et al. |
| 10,433,566 B1 * | 10/2019 | Falgout ................ A22C 29/026 |
| 2013/0241574 A1 * | 9/2013 | Burke ................ G01N 27/023 |
| | | 324/633 |
| 2016/0232656 A1 | 8/2016 | Taylor et al. |
| 2017/0035069 A1 | 2/2017 | Ledet et al. |

FOREIGN PATENT DOCUMENTS

| | | |
|---|---|---|
| WO | 98/17406 A1 | 4/1998 |
| WO | 2006/058406 A1 | 6/2006 |

* cited by examiner

SHRIMP PROCESSING SYSTEM

BACKGROUND

The invention relates to the processing of raw shrimps, including the automated visual inspection of a continuous stream of shrimps and the diversion of rejects.

In the shrimp-processing industry, raw shrimps are peeled by machine and the shells discarded. But some of the shrimps exit the peeling machine with residual shell. Other of the shrimps are damaged in the peeling machine and broken into bits. Shrimp bits and shrimps with residual shell are undesirable in the final product.

SUMMARY

A shrimp processing system embodying features of the invention comprises an imaging chamber and a conveyor conveying a stream of shrimps from an infeed end to a discharge end through the imaging chamber. The imaging chamber includes a UV source continuously subjecting an exposure region of the conveyor in the imaging chamber to ultraviolet radiation, a white-light source turned on and off periodically to subject the exposure region to white light only when the white-light source is turned on, and a camera imaging the exposure region to take a first image of the shrimps on the conveyor when the white-light source is turned on and a second image when the white-light source is turned off. A controller turns the white-light source on and off and processes the first and second images to identify shrimps to be rejected as rejects.

A method for processing shrimps comprises: a) conveying shrimps through an imaging chamber; b) illuminating the imaging chamber continuously with ultraviolet radiation; c) turning a white-light source on to illuminate shrimps being conveyed through an exposure region; d) taking a white-light image of the shrimps in the exposure region; e) turning the white-light source off after the white-light image is taken; f) taking an ultraviolet image of the shrimps in the exposure region; and g) repeating steps c) through f) periodically.

DETAILED DESCRIPTION

Figure 1:
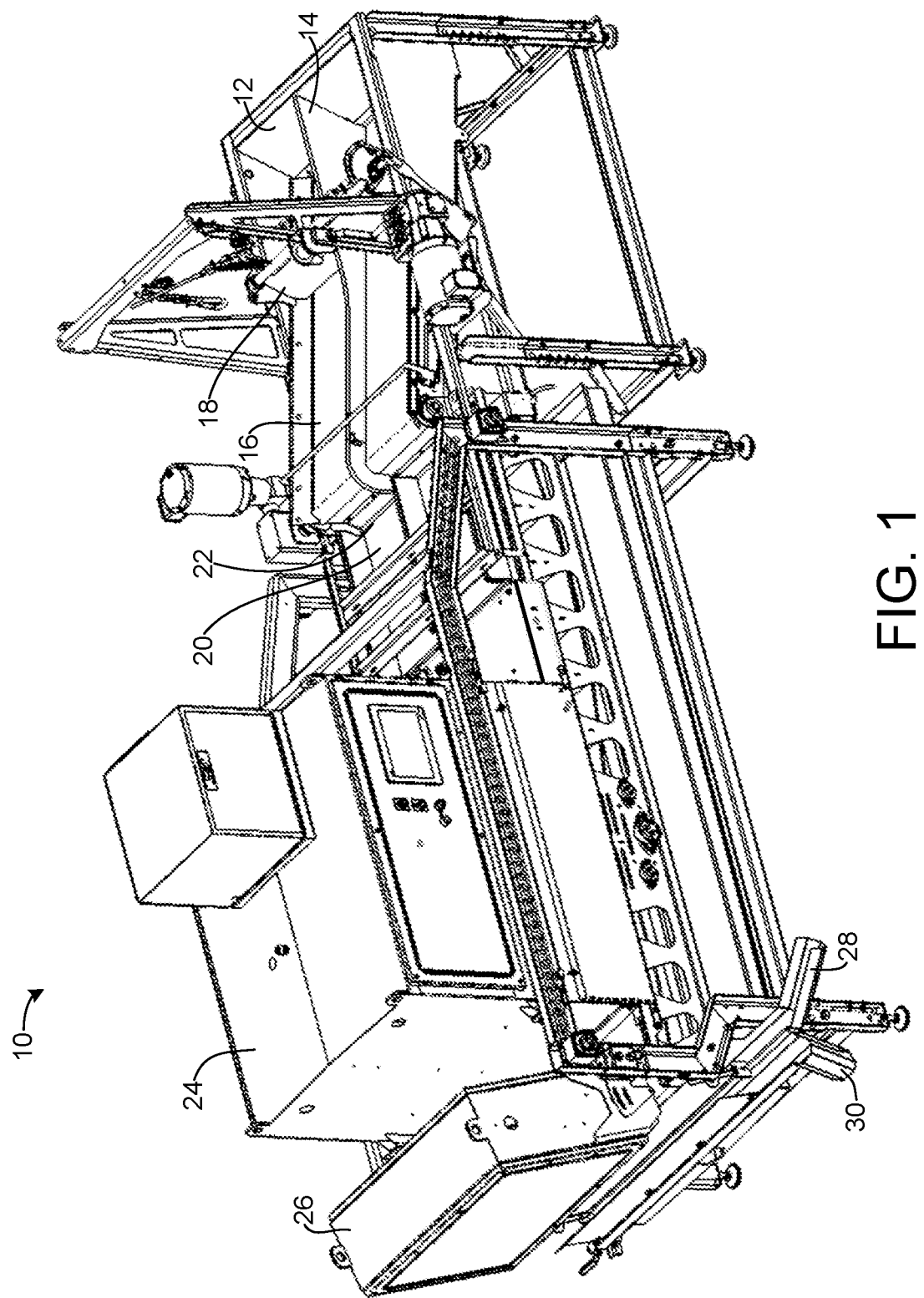
FIG. 1 is an isometric view from above of the imaging and inspection portion of a shrimp processing system embodying features of the invention.

The imaging and inspection portion of a shrimp processing system is shown in FIG. 1. The shrimp processing system 10 in this example version receives raw shrimps peeled in a water-filled tank 12 separated into two halves by a divider 14. But in other versions, the tank 12 need not be water-filled or have a divider. The shrimps are peeled by one or more automated peeling machines upstream of the tank 12. The shrimps are distributed in uniform layers on inclined conveyor belts 16 by reciprocating paddles 18. The bottom upstream ends of the belts 16 are in the tank 12. The shrimps on the inclined conveyor belts 16 drop off upper ends onto another conveyor 20 at its upstream infeed end 22. The drop helps separate the shrimps from one another. The conveyor 20, such as a belt conveyor, is normally run at a greater speed than the inclined belts 16 to further separate the shrimps. Although, in this example, two inclined conveyor belts 16 are used, a single conveyor belt or even another kind of infeed could be used to deliver shrimps to the conveyor 20.

The conveyor 20 conveys the stream of generally separated shrimps through an imaging chamber 24 that prevents outside ambient light from entering. The shrimps on the conveyor 20 are imaged under visible light, such as white light, and under ultraviolet (UV) radiation in the imaging chamber. From the white-light and UV images, a visual inspection system identifies rejects— (a) shrimps with residual shell and (b) bits, i.e., shrimp pieces smaller than a predetermined or user-settable size—and their positions on the conveyor. A controller uses the identification and positional information from the visual inspection system to control air-jet nozzles in an ejector module 26 to blow rejects of a first kind, e.g., shrimps with residual shell, from the stream of shrimps to a first reject destination 28, shown in FIG. 1 as a flume, and to blow rejects of a second kind, e.g., bits, to a second reject destination 30, also shown as a flume. Conveyance means other than flumes, such as belt conveyors, tubes, or chutes, can be used instead. The residual-shell rejects are carried by the first flume 28 back to the upstream peeling machine for re-peeling to detach residual shell. The rejected bits are carried by the second flume 30 to be collected as animal feed or for other uses. Shrimps not rejected are not diverted from the stream and fall off a discharge end of the conveyor 20 onto a discharge conveyor for further processing, such as deveining and inspection.

Figure 2:
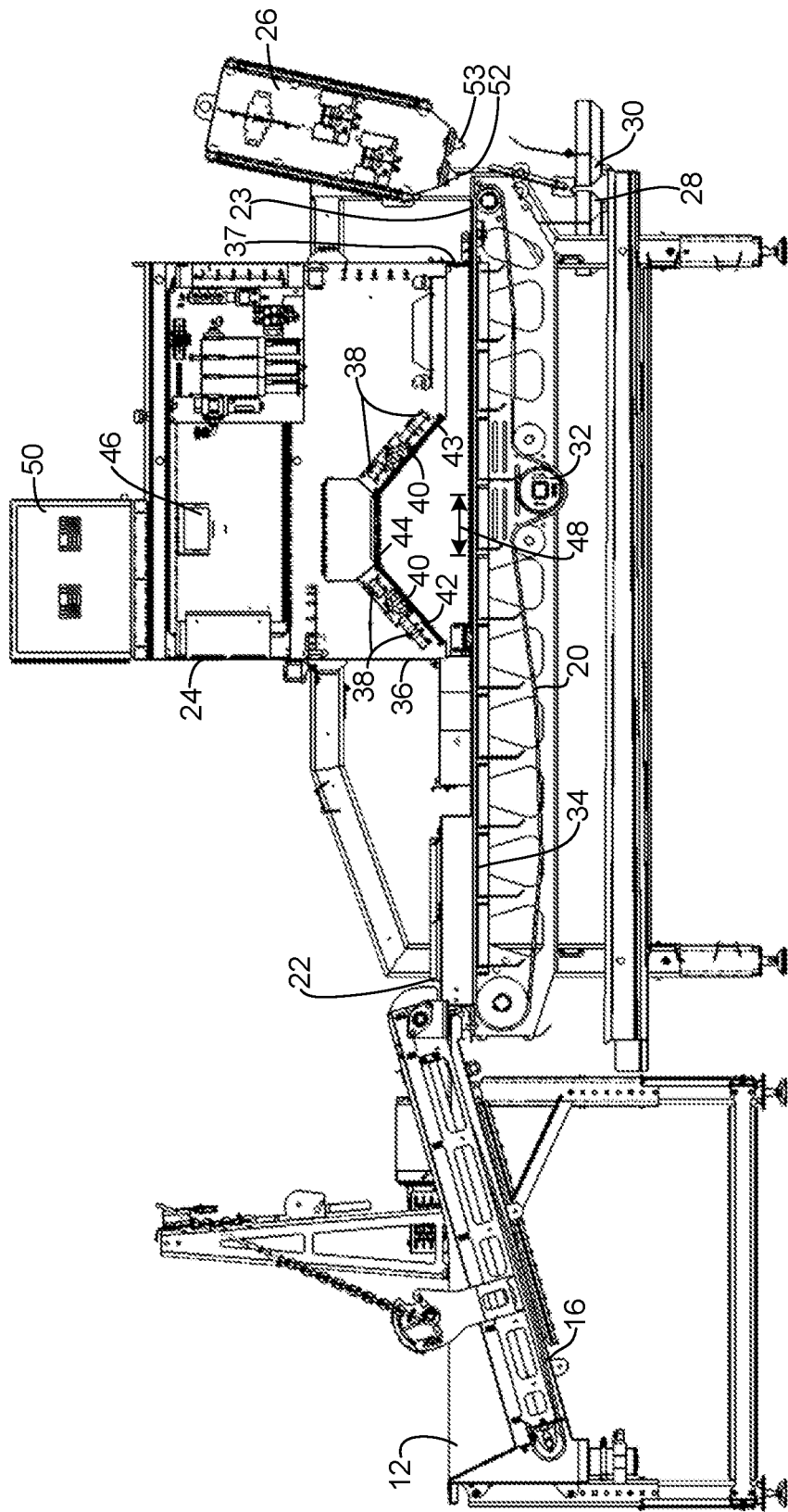
FIG. 2 is a side elevation view of the shrimp processing system of FIG. 1 with the facing side open.

More details of the imaging and sorting portion of the shrimp processing system are shown in FIG. 2. Shrimps conveyed out of the tank 12 on the inclined conveyor belts 16 drop onto the infeed end 22 of the belt conveyor 20. The belt conveyor 20 is driven by a motor-driven drive shaft and sprocket set 32 in the belt's lower return run. The upper run of the belt conveyor 20 is supported in a carryway 34 that extends from the infeed end 22 to an opposite discharge end 23. The conveyor 20 conveys the stream of shrimps continuously through the imaging chamber 24 from an entrance 36 to an exit 37.

Housed in the imaging chamber 24 are a white-light source 38, such as arrays of light-emitting diodes, and a UV source 40. In the examples of FIG. 2, the sources 38, 40 are mounted on leading and trailing plates 42, 43 angled downward away from a central plate 44 and extending across the width of the belt conveyor 20. The central plate includes an opening through which a camera in a visual inspection system 46 captures an image from an exposure region 48 on the belt conveyor 20. (One example of a visual inspection system is the SiftAI® system sold by Smart Vision Works of Orem, Utah, U.S.A.) A temperature control system 50, e.g., an air conditioner, including a temperature sensor adjacent the UV source 40, maintains the temperature of the air around the UV source generally constant at a temperature within a predetermined range, e.g., between 0° F. and 150° F., to prevent the intensity of the UV radiation from varying more than is acceptable.

The belt conveyor 20 conveys the shrimps off its discharge end 23. As the shrimps fall from the conveyor 20, air-jet nozzles in the ejector module 26 arranged in two rows 52, 53 are individually and selectively actuated to blow rejects of the first kind and rejects of the second kind from the stream of falling shrimps into the first and second reject destinations 28, 30. The rest of the falling shrimps drop onto a discharge conveyor (not shown) for further processing.

Figure 3:
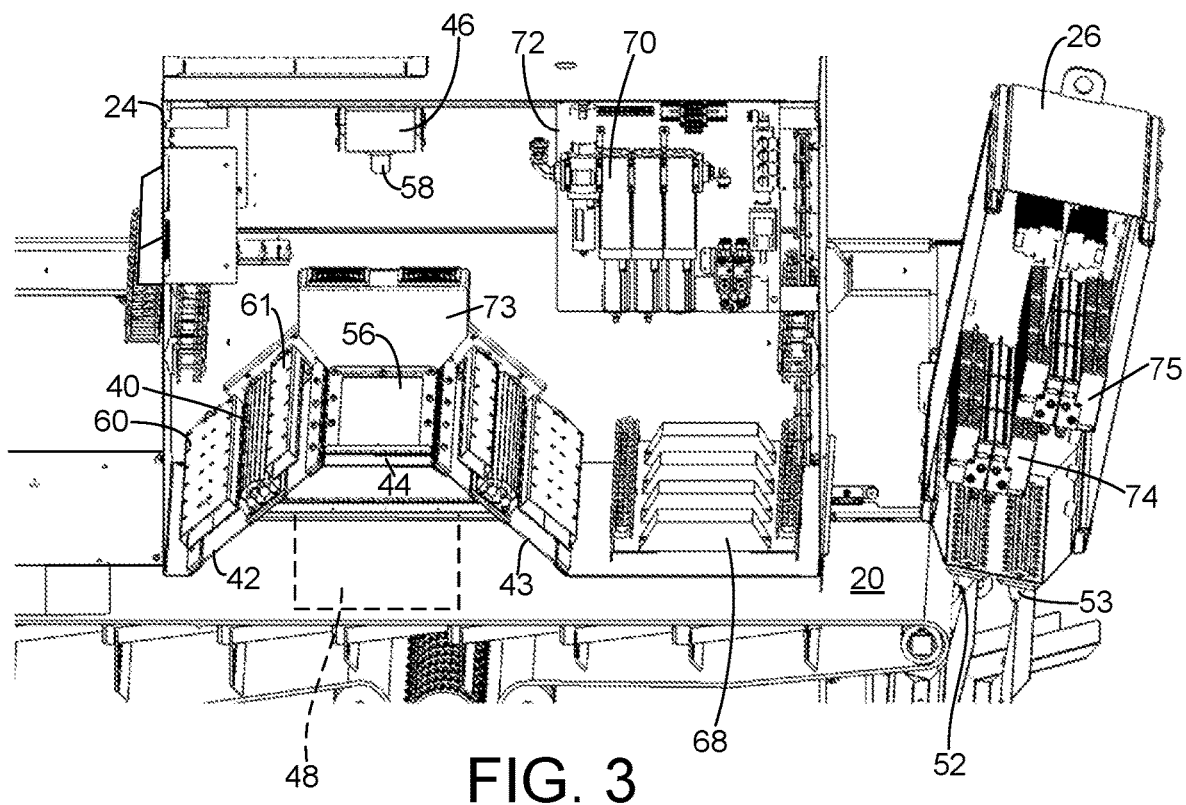
FIG. 3 is an enlarged view of a portion of the shrimp processing system of FIG. 2.
Figure 4:
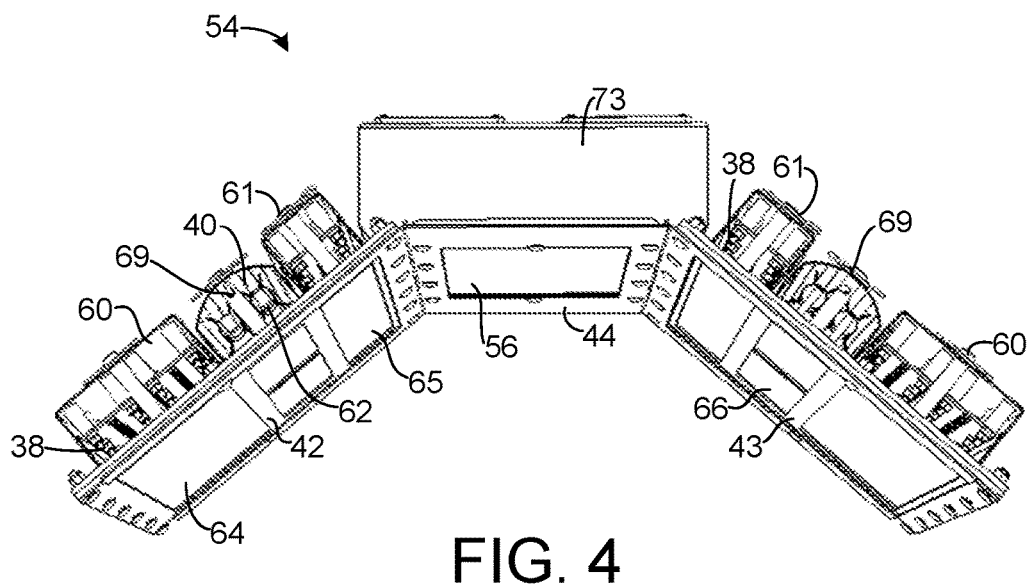
FIG. 4 is a further enlarged view of the lighting system of the shrimp processing system of FIG. 3.

As shown in FIGS. 3 and 4, the lighting system 54 comprises three plates 42, 43, 44 above the belt conveyor 20. The central plate 44, which is parallel to the plane of the belt conveyor 20, has a window 56 through which a camera 58 in the visual inspection system 46 images the exposure region 48 on the conveyor 20. The two flanking plates 42, 43 are mirror images of each other. Each plate 42, 43 supports two sets 60, 61 of white-light sources 38, such as light-emitting diode (LED) arrays. Between the white-light sources 60, 61 in each flanking plate 42, 43 is a UV source 40, such as a pair of $UV_c$ tubes 62. The flanking plates 42, 43 include cutouts for diffusers 64, 65 for the LED arrays and for bandpass filters 66 for the UV tubes 62. The bandpass filters confine the $UV_c$ energy illuminating the exposure region 48 to a narrow frequency band. The diffusers 64, 65 diffuse the white LED light shining on the exposure region 48. Other arrangements of the white-light sources 60, 61 and the UV tubes 62 are possible.

Also housed in the imaging chamber 24 are ballasts 68 for the UV tubes 62, air filters and a compressor 70 (generally) for the air-jet nozzles, and circuit boards 72 for the controller, power supplies, and other support circuitry. An air duct 73 directs cooled air from the temperature control system 50 to the UV sources 40 to maintain their temperature. A temperature sensor 69 near each UV source 40 provides temperature feedback to the closed-loop temperature control system. Because the UV tubes are relatively slow to power up, the UV source is left on continuously rather than turned off and on to ensure a consistent radiation intensity for imaging.

The ejector module 26 houses two arrays of valves 74, 75 that are controlled by the controller to selectively supply bursts of air to corresponding air-jet nozzles 52, 53 to divert rejects from the stream of shrimps exiting the belt conveyor 20.

Figure 6:
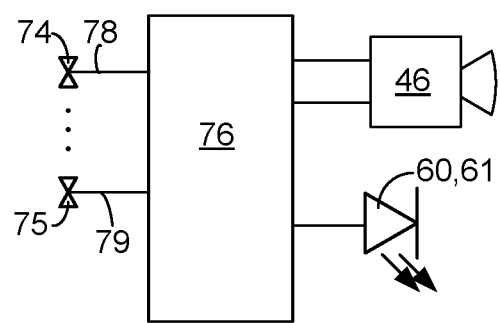
FIG. 6 is a block diagram of a control for a shrimp processing system as in FIG. 1.

A block diagram of a control for the imaging and inspection system is shown in FIG. 6. A controller 76, such as a programmable logic controller or other programmable processor executing program steps in a program memory, controls the timing and receives imaging information from the visual inspection system 46. The controller 76 also turns on and off the white-light source 60, 61 for the white-light imaging. The controller 76 activates each of the air-jet valves 74, 75 over control lines 78, 79.

Figure 5:
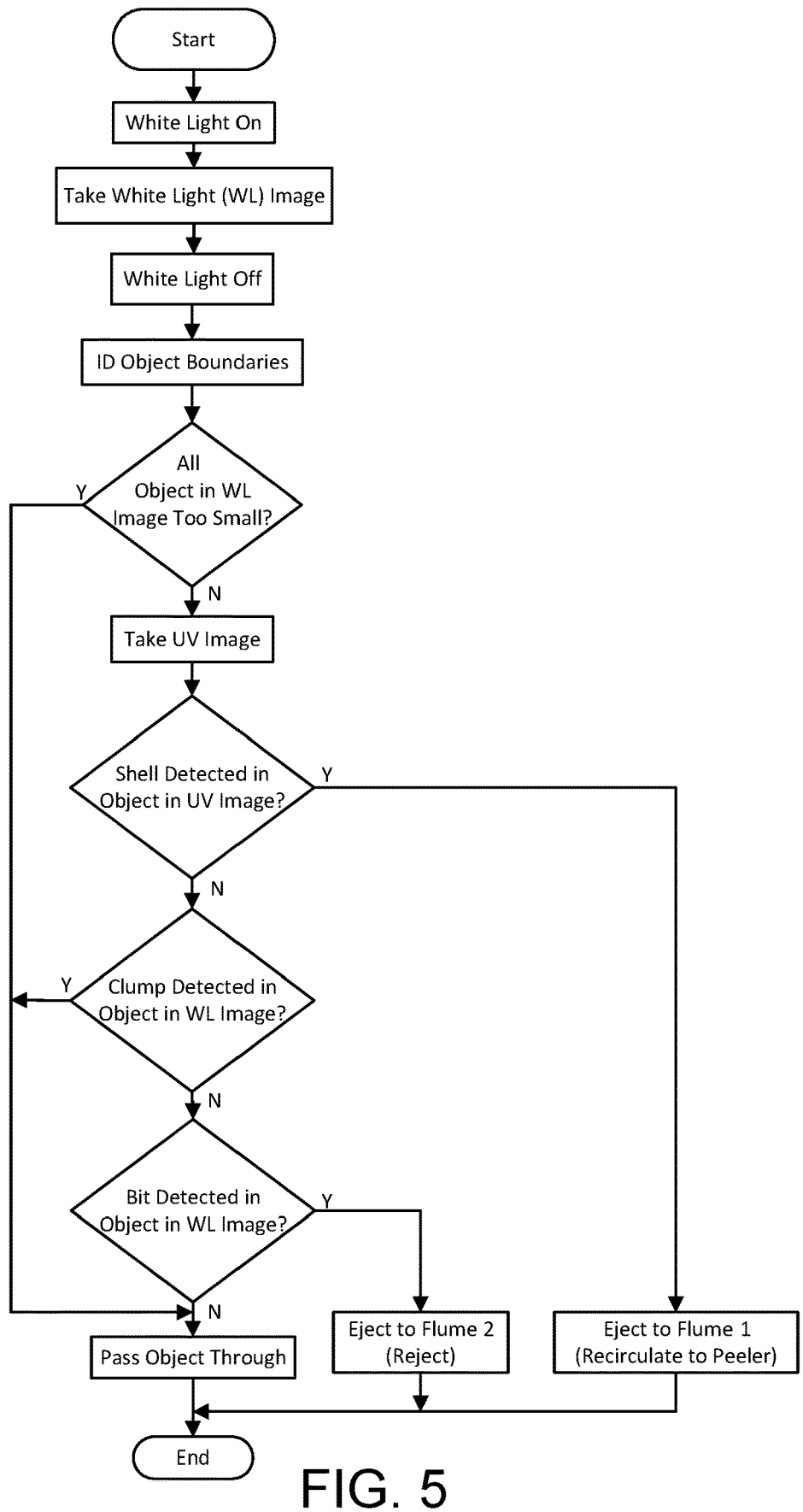
FIG. 5 is a flowchart exemplifying the operation of the imaging and inspection portion of the shrimp processing system of FIG. 1.

A flowchart of an example implementation of one cycle of the imaging, inspection, and sorting process is shown in FIG. 5. First, the controller turns the white-light source on. Then the controller commands the visual inspection system to take the white-light images of the exposure region on the conveyor. The controller then turns the white-light source off. Although the UV source is on continuously, its intensity level is enough below the intensity of the white light that it does not affect the white-light image. After the white-light image is taken, the visual inspection system identifies the boundaries of objects in the exposure region of the conveyor. If the object boundaries enclose an area of less than a predetermined or user-settable number of pixels, the object is considered too small to be a significant piece of shrimp meat and is ignored.

All objects whose boundaries exceed that number of pixels are considered pieces of shrimp meat and their position in the exposure region of the conveyor saved. If no objects large enough to be considered pieces of shrimp meat are in the image, the inspection cycle is ended. If any objects in the white-light image are large enough, the visual inspection system takes a UV image with the white-light source turned off. Any shell present on a shrimp fluoresces under the $UV_c$ radiation and is detected in the UV image captured by the visual inspection system. The detected shell is associated with an object detected in the white-light image. The position of the shrimp with residual shell is sent to the controller by the visual inspection system so that the controller can eject that object to a first reject flume to be recirculated back through the upstream peeling machine.

If a large object has no detected shell, the visual inspection system further processes the object's white-light image to determine if the object is a shrimp bit (a piece of shrimp meat whose boundary encloses an area smaller than an area corresponding to a predetermined minimum shrimp size), a clump of shrimps (multiple overlapping shrimps whose combined size defines a boundary enclosing an area that exceeds an area corresponding to a maximum shrimp size), or an acceptable shrimp. If an object is classified as a clump, it is not treated as a reject. A bit, on the other hand, is treated as a reject of a second kind destined for ejection to a second reject flume. Acceptable shrimp and clumps are both allowed to pass through without diversion to a discharge conveyor for further downstream processing.

The visual inspection system sends image information that includes the position of rejects of the first kind (shrimps with residual shell) and of the second kind (bits) to the controller. The controller, with knowledge of the conveyor speed and the rejects' positions on the conveyor, controls the air-jet valves to eject rejects of the first kind to the first flume and rejects of the second kind to the second flume. The visual inspection system also sends counts of the number of bits, the number of clumps, the number of shrimps with residual shell, and the number of acceptable shrimps to the controller for statistical analysis.

Although the shrimp processing system has been described in detail with respect to an exemplary version, other versions are possible. For example, characteristics other than bits and residual shell could be classified as defects, and objects with those characteristics diverted from the stream of acceptable shrimps. Clumps are one example. Other examples are objects recognized as small fish, pieces of debris, and unrecognized objects. So as these examples suggest, the claims are not meant to be limited to the details of the exemplary version.

What is claimed is:

1. A shrimp processing system comprising:
   an imaging chamber;
   a conveyor having a width, an infeed end, and an opposite discharge end and conveying a stream of shrimps from the infeed end to the discharge end and through the imaging chamber;
   wherein the imaging chamber includes:
   a UV source continuously subjecting an exposure region of the conveyor in the imaging chamber to ultraviolet radiation;
   a white-light source turned on and off periodically to subject the exposure region to white light only when the white-light source is turned on;
   a camera imaging the exposure region to take a first image of the shrimps on the conveyor when the white-light source is turned on and a second image when the white-light source is turned off;

a controller turning the white-light source on and off and processing the first and second images to identify shrimps to be rejected as rejects.

2. The shrimp processing system of claim 1 comprising:

a plurality of air-jet nozzles proximate the discharge end of the conveyor;

wherein the controller controls the air-jet nozzles to selectively direct jets of air at the rejects exiting the discharge end of the conveyor to divert the rejects from the stream of shrimps to one or more reject destinations.

3. The shrimp processing system of claim 2 wherein the controller identifies shrimps with residual shell as rejects from the second image and controls the air-jet nozzles to direct jets of air at the shrimps with residual shell to a first reject destination.

4. The shrimp processing system of claim 3 comprising an automated shrimp-peeling machine upstream of the imaging chamber peeling shrimps and wherein the first reject destination includes a flume recirculating the shrimps with residual shell to the automated shrimp-peeling machine to be re-peeled.

5. The shrimp processing system of claim 2 wherein the controller identifies shrimp bits as rejects from the first image and controls the air-jet nozzles to direct jets of air at the shrimps with residual shell to a second reject destination.

6. The shrimp processing system of claim 1 wherein the controller identifies clumps not as rejects from the first image and allows the clumps to pass with the stream of shrimps without being diverted.

7. The shrimp processing system of claim 1 comprising a temperature control system including a temperature sensor for maintaining the temperature of the UV source within a narrow range to prevent the intensity of the ultraviolet radiation from varying.

8. The shrimp processing system of claim 1 wherein the plurality of air-jet nozzles are arranged in two parallel rows spanning the width of the conveyor and wherein a first row of the two rows diverts rejects of a first kind to a first reject destination and the second row of the two rows diverts rejects of a second kind to a second reject destination.

9. A method for processing shrimps comprising:

a) conveying shrimps through an imaging chamber at a conveyor speed;

b) illuminating the imaging chamber continuously with ultraviolet radiation;

c) turning a white-light source on to illuminate shrimps being conveyed through an exposure region in the imaging chamber;

d) taking a white-light image of the shrimps in the exposure region;

e) turning the white-light source off after the white-light image is taken;

f) taking an ultraviolet image of the shrimps in the exposure region while the white-light source is turned off; and g) repeating steps c) through f) periodically.

10. The method of claim 9 comprising identifying the positions and the boundaries of the shrimps and other objects in the exposure region from the white-light image.

11. The method of claim 10 comprising:

classifying objects whose boundaries enclose an area less than a first area as bits; and diverting the bits from the rest of the shrimps.

12. The method of claim 10 comprising classifying objects whose boundaries enclose an area greater than a second area as clumps.

13. The method of claim 10 comprising controlling air jets to divert selected shrimps and other objects after exiting the imaging chamber from their positions in the imaging chamber and the conveyor speed.

14. The method of claim 9 comprising:

identifying shell on the shrimps from the ultraviolet image; and diverting the shrimps with shell from rest of the shrimps.

15. The method of claim 14 comprising:

peeling shrimps in an automated shrimp-peeling machine before conveying the shrimps through the imagine chamber; and recirculating the shrimps with shell diverted from the rest of the shrimps back to the automated shrimp-peeling machine to be re-peeled.

16. The method of claim 9 comprising classifying shrimps as rejects or acceptable shrimps from the white-light images and the ultraviolet images and diverting rejects from the acceptable shrimps.

17. The method of claim 16 comprising classifying shrimps with residual shell identified from the ultraviolet image and shrimps whose boundaries enclose areas less than a minimum shrimp-size area as rejects.

18. The method of claim 16 comprising diverting the rejects from the acceptable shrimps after exiting the imaging chamber with air jets.

* * * * *